United States Patent [19]

Krevald et al.

[11] Patent Number: 4,719,103
[45] Date of Patent: Jan. 12, 1988

[54] METHOD FOR THE PREPARATION OF WATER-IN-OIL EMULSION ANTIPERSPIRANTS

[75] Inventors: Helga Krevald, Tarrytown, N.Y.; Joseph C. Hourihan, Little Falls, N.J.

[73] Assignee: American Cyanamid Company, Stamford, Conn.

[21] Appl. No.: 815,187

[22] Filed: Dec. 23, 1985

Related U.S. Application Data

[63] Continuation of Ser. No. 621,122, Jun. 13, 1984, abandoned, which is a continuation of Ser. No. 353,731, Mar. 1, 1982, abandoned.

[51] Int. Cl.$^4$ .......................... A61K 7/34; A61K 7/38
[52] U.S. Cl. .................. 424/66; 424/DIG. 5; 424/68
[58] Field of Search ....................... 424/68, 66, DIG. 5

[56] References Cited

U.S. PATENT DOCUMENTS

| | | | |
|---|---|---|---|
| 3,341,465 | 9/1967 | Kaufman et al. | 424/69 |
| 4,021,536 | 5/1977 | Rubino | 424/47 |
| 4,265,878 | 5/1981 | Keil | 424/68 |
| 4,268,499 | 5/1981 | Keil | 424/68 |
| 4,350,605 | 9/1982 | Hughett | 424/68 |

OTHER PUBLICATIONS

Ash et al., A Formulary of Cosmetic Preparations, 1977, pp. 10 to 17, 22 and 23.

*Primary Examiner*—Dale R. Ore
*Attorney, Agent, or Firm*—C. J. Fickey

[57] ABSTRACT

Method for making an antiperspirant composition of the water-in-oil emulsion type having improved application properties and aesthetic appeal which comprises emulsifying the aqueous phase in the oil phase in the presence of from 1 to 3% by weight of a non-ionic surfactant having a resultant HLB value in the range of 6 to 9.

5 Claims, No Drawings

METHOD FOR THE PREPARATION OF WATER-IN-OIL EMULSION ANTIPERSPIRANTS

This application is a continuation of application Ser. No. 621,122, filed June 13, 1984, which is a continuation of Ser. No. 353,731, filed Mar. 1, 1982, both now abandoned.

The present invention relates to improvements in water-in-oil emulsions. More particularly, it relates to improvements in the preparation of water-in-oil emulsion type antiperspirant compositions. Still more particularly, it relates to improvements in antiperspirant compositions, especially antiperspirant sticks, which result when an aqueous solution of an antiperspirant astringent is emulsified in a waxy hydrophobic matrix which may contain a volatile silicone liquid.

Water-in-oil emulsion type antiperspirant sticks are known, but they have not met with much success. This is due, primarily, to the fact that they have poor application properties, that is, they exhibit a draggy feel when applied. Moreover, they are not very efficacious and they lack aesthhetic appeal. Nevertheless, there has been a trend toward antiperspirant compositions which exhibit a "dry" feel and a number of compositions have been reported, both suspension types and water-in-oil emulsion types, which comprise a volatile silicone liquid to provide the dry feel.

Gee et al, U.S. Pat. No. 4,122,029, and Keil, U.S. Pat. No. 4,265,878, describe water-in-oil emulsion type antiperspirant sticks in which an aqueous solution of an astringent, such as aluminum chlorohydrate, is emulsified in a hydrophobic continuous phase, for example, a volatile silicone. Gee et al use a silicon-free water-in-oil surfactant having an HLB value of 2 to 10 and certain polydiorganosiloxane-polyoxyalkylene block copolymers as emulsifying agents. Keil discloses that the primary surfactant, that is, the polydiorganosiloxane-polyoxyalkylene block copolymers, and the volatile silicone liquid, are more compatible with a wax base comprising a solid alkanoic acid (for example, stearic acid), a waxy ester (for example, spermaceti wax) and, optionally, a solid alkanol in limited amounts, than they are with the conventionally used solid alkanols.

Cosmetic sticks of the water-in-oil emulsion type are also disclosed by Fujiyama et al, British Pat. No. 1,442,426. These sticks, which are primarily lipsticks, are reported to have improved moistening, spreadability, and lustering properties. Essentially, Fujiyama's compositions comprise water, a polyhydroxy compound (for exampe, mannitol, glycerol), a non-ionic surfactant selected from oleic acid esters and oleyl ethers of polyhydric alcohols, and a cosmetic base (for example, a wax).

The preparation of water-in-oil emulsions, as in Fijiyama et al, has typically involved the use of a non-ionic oleic acid ester or oleyl ether of a polyhydric alcohol as the emulsifying agent. These include such commonly used surfactants as glycerol monooleate, sorbitol monooleate, glycerol dioleate, and the like. These unsaturated esters and ethers, when used to prepare water-in-oil emulsion type antiperspirant sticks, tend to result in rancidity.

Thus, there is a need for a method for the preparation of water-in-oil emulsion type antiperspirant compositions which exhibit improved application properties and aesthetic appeal.

In accordance with the present invention, it has been found that if a water-in-oil emulsion type antiperspirant composition is prepared using a low concentration of a saturated or unsaturated non-ionic surfactant, having an HLB value of 6 to 9, the resulting emulsion will be near the breaking point and will break at the time of application, or slightly thereafter, to provide enhanced application properties and more efficient delivery of the astringent to the axilla.

It is believed that it is necessary for the emulsion to break at the time of application of the antiperspirant, or soon thereafter, in order for the active astringent to be effective in reducing perspiration.

It is, therefore, desirable to provide a water-in-oil emulsion which is near the breaking point. This is accomplished, in accordance with the invention, by carefully selecting the emulsifying agent, or agents, so that the resultant HLB value will be in the range of about 6 to 9. If the HLB value is appreciably below about 6, the antiperspirant stick will have a draggy feel on application; if the HLB value is appreciably higher than about 9, the emulsion will invert to an oil-in-water type and the antiperspirant will have a tacky feel.

The amount of emulsifier used should be in the range of about 1 to 3% by weight, based on the weight of the composition. It is important that the concentration used will be such as to achieve an emulsion which is near the breaking point. Of course the concentration will be dependent on the type of oils and waxes used in the hydrophobic phase. If too little is used, the emulsion will not form or will be unstable; if too much is used, the emulsion will not break readily and will not release the astringent efficiently.

Although the present invention will be described with respect to the preparation of a wter-in-oil emulsion type antiperspirant stick, it will be recognized that water-in-oil emulsion type antiperspirants may take other forms, such as creams and lotions, and that the method of the invention is applicable to the preparation of water-in-oil emulsions in general and to their use in other products, such as lipsticks, pharmaceutical preparations, and the like.

Essentially, in the preparation of water-in-oil emulsion type antiperspirant sticks, an aqueous solution of an antiperspirant astringent compound is emulsified, by conventional emulsification techniques, in a hydrophobic medium by the use of a suitable emulsifying agent.

The term "hydrophobic medium," as used herein, means any of the water-insoluble oils, waxes, fatty alcohols, fatty acid esters, fatty acid amides, metal salts of alkanoic acids, volatile silicones, and the like, commonly used in the cosmetic art to prepare cosmetic emulsions, so long as they are compatible with each other and with the emulsifying agent. In the present invention, a preferred hydrophobic medium is a waxy matrix comprising a volatile cyclic polydimethyl siloxane oligomeric liquid, often referred to in the art as a volatile silicone.

The cyclic tetramer (I, 2,4,6,8-octamethylcyclotetrasiloxane), cyclic pentamer (II, 2,4,6,8,10-decamethylcyclopentasiloxane), and cyclic hexamer (III, 2,4,6,8,10,12-dodecamethylcyclohexasiloxane), and mixtures thereof, are commonly available commercially (Dow Corning).

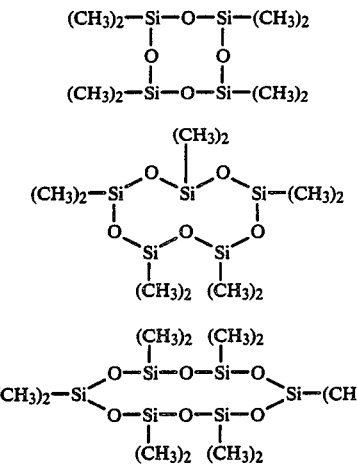

The waxy matrix may comprise any of the waxes or wax-like compounds commonly used in sticks, but preferably the waxy matrix of the present invention will comprise a solid fatty alcohol, such as stearyl alcohol or cetyl alcohol, or mixtures thereof, and, optionally, a solid alkanoic acid, for example, stearic acid.

Other commonly used ingredients may be incorporated into the composition to achieve certain desirable effects, such as mineral oil, other emollients, fragrances, dyes, and the like.

Among the useful astringents are aluminum sulfate, aluminum chloride, aluminum chlorohydrate, aluminum sulfocarbolate, aluminum-zirconium chlorohydrate, zinc chloride, zinc sulfocarbolate, zinc sulfate, zirconium salts, such as zirconium chlorohydrate, combinations of aluminum chloride and aluminum chlorohydrate or aluminum-zirconium chlorohydrate, aluminum-zirconium chlorohydroglycine, and the like. Aluminum chlorohydrate as a 50% aqueous solution is preferred.

The active ingredient may be used in amounts up to about 30% by weight on a solids basis although normally used range from about 15 to 25% by weight, on a solids basis. In any case, sufficient should be used to achieve at least a 20% reduction in perspiration in 50% of the population.

The emulsifying agents useful in the invention are saturated or unsaturated compounds or a mixture of compounds having a resultant HLB value (calculated according to the method described in "The Atlas HLB System," Communique, Atlas Chemical Industries, Inc., 4th Printing) of 6 to 9. A preferred type of emulsifying agent are the saturated fatty acid esters of polyglycerol, for example, polyglyceryl-4-isostearate, which is the isostearic acid ester of polyglycerol having 4 repeating units in the oligomeric chain. In general the preferred emulsifying agents are long chain ($C_{12}$–$C_{20}$) saturated esters of polyglycerol containing from about 2 to 10 repeating glycerol units, preferably 3 to 6 units, in the oligomeric chain.

Any saturated or unsaturated non-ionic surfactant, or combination of surfactants, having a resultant HLB value in the range of 6 to 9 will also provide water-in-oil emulsion type antiperspirants in accordance with the invention.

The following water-in-oil emulsion antiperspirant stick compositions were prepared using emulsifying agents having a resultant HLB value in the range of 6–9. All have good application properties and good antiperspirant properties.

EXAMPLE 1

|  | Percent by Weight |
|---|---|
| Aluminum chlorohydrate, 50% aq. soln. | 43.0 |
| Cyclic silicone pentamer | 26.0 |
| Stearyl alcohol | 17.0 |
| Stearic acid | 2.0 |
| Polyglyceryl-4-isostearate (Witcanol 18L) | 2.0 |
| 2-Methyl-2,4-pentanediol | 4.0 |
| Mineral oil | 1.0 |
| Water | 5.0 |
|  | 100.0 |

EXAMPLE 2

|  | Percent by Weight |
|---|---|
| Aluminum chlorohydrate, 50% aq. soln. | 45.0 |
| Cyclic silicone pentamer | 24.0 |
| Stearyl alcohol | 17.0 |
| Stearic acid | 2.0 |
| Water | 3.0 |
| Polyglyceryl-4-isostearate | 2.0 |
| Silicone wax Q5-0158A (Dow Corning) | 3.0 |
| PPG Myristyl propionate (Croda) | 1.0 |
| 2-Methyl-2,4-pentanediol | 2.0 |
| Polyethylene 617A (Allied) | 0.5 |
| Fragrance | 0.5 |
|  | 100.0 |

EXAMPLE 3

|  | Percent by Weight |
|---|---|
| Aluminum chlorohydrate, 50% aq. soln. | 45.0 |
| Cyclic silicone pentamer | 25.9 |
| Stearyl alcohol | 17.0 |
| Stearic acid | 2.0 |
| 2-Methyl-2,4-pentanediol | 2.0 |
| Polyglyceryl-4-isostearate | 1.7 |
| Glyceryl oleate + propylene glycol (Arlacel 186) | 1.3 |
| PPG Myristyl ether (Witcanol APM) | 1.0 |
| Polyethylene 617 A | 1.1 |
| Water | 3.0 |
|  | 100.0 |

EXAMPLE 4

|  | Percent by Weight |
|---|---|
| Aluminum chlorohydrate, 50% aq. soln. | 50.0 |
| Cyclic silicone pentamer | 26.0 |
| Stearyl alcohol | 19.0 |
| Polyglyceryl-4-oleate (Witcanol 14) | 2.0 |
| 2-Methyl-2,4-pentanediol | 2.0 |
| Mineral oil | 1.0 |
|  | 100.0 |

EXAMPLE 5

|  |  |
|---|---|
| Al Zirconium chlorhydrex | 25.0 |
| Deionized Water | 25.0 |
| Cyclic silicone pentamer | 22.0 |
| Stearyl alcohol | 20.0 |
| Hexylene glycol | 3.0 |
| Polyglyceryl 4 isostearate | 1.5 |
| Polyglyceryl 3 diisostearate | 1.5 |

| -continued | |
|---|---|
| Stearic acid | 2.0 |
| | 100.0 |

What is claimed is:

1. In an antiperspirant stick composition of the water-in-oil emulsion type consisting essentially of,
   (a) 10 to 70 parts by weight of an aqueous solution of an astringent compound as a discontinuous phase dispersed in a solid matrix consisting essentially of,
   (b) 0.1 to 35 parts be weight of a volatile cyclic dimethylsiloxane liquid,
   (c) 10 to 30 parts by weight of at least one solid alkanol containing at least 12 carbon atoms,
   (d) 1 to 5 parts by weight of a $C_4$ to $C_8$ alkanediol,
   (e) wherein the improvement comprises 0.5 to 5 parts by weight of at lease one $C_{12}$ to $C_{20}$ fatty acid ester of a polyglycerol, said ester having a resultant HLB value of 6 to 9 to improve the application aesthetics; the total of (a) through (e) being 100 parts by weight.

2. A composition according to claim 1 wherein said hydrophobic phase comprises a volatile cyclic polydimethyl siloxane liquid.

3. A composition according to claim 1 wherein said hydrophobic phase is a waxy matrix comprising a volatile cyclic polydimethyl siloxane liquid.

4. A composition according to claim 3 wherein waxy matrix additonally comprises a solid fatty alkanol.

5. A composition according to claims 1 to 4 wherein said emulsifying agent is a $C_{12}$ to $C_{20}$ saturated ester of polyglycerol containing from about 2 to 10 repeating glycerol units.

* * * * *